United States Patent
Ashton

(10) Patent No.: US 10,413,396 B2
(45) Date of Patent: Sep. 17, 2019

(54) TOOL AND METHOD FOR CRIMPING FABRIC

(71) Applicant: VASCUTEK LIMITED, Renfrewshire (GB)

(72) Inventor: Timothy Rawden Ashton, Ayrshire (GB)

(73) Assignee: VASCUTEK LIMITED, Renfrewshire (GB)

( * ) Notice: Subject to any disclaimer, the term of this patent is extended or adjusted under 35 U.S.C. 154(b) by 445 days.

(21) Appl. No.: 15/038,163

(22) PCT Filed: Nov. 13, 2014

(86) PCT No.: PCT/GB2014/053367
§ 371 (c)(1),
(2) Date: May 20, 2016

(87) PCT Pub. No.: WO2015/075425
PCT Pub. Date: May 28, 2015

(65) Prior Publication Data
US 2016/0287375 A1    Oct. 6, 2016

(30) Foreign Application Priority Data
Nov. 22, 2013    (GB) .................................. 1320661.0

(51) Int. Cl.
*A61F 2/07* (2013.01)
*A61F 2/95* (2013.01)
(Continued)

(52) U.S. Cl.
CPC .................. *A61F 2/07* (2013.01); *A61F 2/95* (2013.01); *D02G 1/004* (2013.01);
(Continued)

(58) Field of Classification Search
CPC .... A61F 2/07; A61F 2/95; A61F 2/962; A61F 2002/9505; A61F 2002/9522;
(Continued)

(56) References Cited

U.S. PATENT DOCUMENTS 5,893,852 A * 4/1999 Morales .................. A61F 2/958
606/108
2008/0213464 A1    9/2008 O'Connor
2013/0197657 A1    8/2013 Anca et al.

FOREIGN PATENT DOCUMENTS

WO    2011084342 A1    7/2011

OTHER PUBLICATIONS

"Chamfer Router Bits", Carbide Processors, Inc, accessed at carbideprocessors.com on Oct. 12, 2018. (Year: 2018).*
(Continued)

*Primary Examiner* — Joseph S Del Sole
*Assistant Examiner* — Jamel M Nelson
(74) *Attorney, Agent, or Firm* — Heslin Rothenberg Farley & Mesiti P.C.; Kristian E. Ziegler

(57) ABSTRACT

A crimping tool is provided, where the tool comprises a mandrel (1) having a first portion (3) with a first outer diameter, and a second portion (5) with a second outer diameter which is greater than the first outer diameter. A chamfered abutment face (7) is provided between the first and second portions (3,5). At least one first collar (9) is mountable on the first portion (3) of the mandrel (5) and has a chamfered first end (11) which in use abuts the abutment face (7). At least one second collar (13) is mountable on the second portion (5) of the mandrel (1) and has a chamfered second end (15) which in use abuts the first end (11) of the first collar (9). A method of using the tool to form one or more crimps in a piece of fabric is also disclosed.

39 Claims, 4 Drawing Sheets

(51) Int. Cl.
*D02G 1/00* (2006.01)
*A61F 2/06* (2013.01)

(52) U.S. Cl.
CPC . *A61F 2002/061* (2013.01); *A61F 2002/9522* (2013.01); *A61F 2230/0067* (2013.01); *A61F 2240/001* (2013.01); *A61F 2250/0065* (2013.01)

(58) Field of Classification Search
CPC ........ A61F 2230/0067; A61F 2240/001; A61F 2250/0065
See application file for complete search history.

(56) References Cited

OTHER PUBLICATIONS

"What is Chamfering and Deburring?", SFGate, accessed at homeguides.sfgate.com on Oct. 12, 2018. (Year: 2018).*
International Search Report for PCT/GB2014/053367 dated Jan. 27, 2015.

* cited by examiner

TOOL AND METHOD FOR CRIMPING FABRIC

CROSS-REFERENCE TO RELATED APPLICATIONS

This application is a national stage filing under section 371 of International Application No. PCT/GB2014/053367, filed on Nov. 13, 2014, and published in English on May 28, 2015 as WO 2015/075425, and claims priority to Great Britain Patent Application No. 1320661.0 filed on Nov. 22, 2013, the entire disclosures of each of the prior applications are hereby incorporated by reference herein The present invention relates to the field of crimping or pleating fabric. More specifically, the present invention provides a tool and method of crimping or pleating fabric which is particularly of use, although not exclusively so, in the manufacture of medical devices used in cardiovascular surgery.

Medical devices such as stent grafts used in cardiovascular surgery are typically woven or knitted from polyester or similar materials. In certain applications a stent graft is required to have one or more fenestrations which will allow branch vessels in the body to be connected to the stent graft and main body lumen within which the graft is deployed. However, no two patients have the exact same arrangement of body lumen and branch vessels. Therefore, in order to provide a single stent graft which can be used with any patient it is known to form stent grafts with fenestrations whose positions upon the graft may be adjusted. This is typically achieved by providing a frustoconical fenestration adjustment region or patch around the fenestration, where this region is made up of an excess of graft fabric. The excess fabric means that the position of the fenestration may be moved within the region relative to the remainder of the stent graft to ensure that the fenestrations are accurately aligned with the branch vessels of the patient.

Whilst the excess fabric of the adjustment region allows for manipulation of the fenestration it can present problems during the compaction and deployment of the stent graft. For example, when the stent graft is compressed within a sleeve or sheath for installation into a patient the behaviour of the excess material is unpredictable. In one instance the excess material may fold in one direction and in another instance it may fold in a different direction. It is therefore difficult for a clinician to predict where the fenestration will lie when the stent graft is deployed following insertion. Furthermore, in some instances the excess material may in fact fold across the fenestration itself, covering and blocking the fenestration entirely. Additionally, depending on how the excess material lies following deployment of the stent graft it may interfere with guide wires or other stenting components if they are to pass the stent graft for use in additional cannulation or stenting operations in branch vessels or elsewhere within the patient.

A solution to the above problems has been to crimp or pleat the adjustment region to ensure the region is as compact as possible during compaction and deployment, and that the behaviour of the region is as predictable as possible. Crimping of these types of medical device has been known for many years. However, as illustrated in the disclosures of U.S. Pat. Nos. 2,836,181 and 3,878,565 the method of crimping used has typically been to apply axial compression to a tubular or cone-shaped device in order to obtain the desired crimps or pleats. A disadvantage of such methods is that uniformity of the pleats is difficult to achieve. This can result in stent grafts and other devices whose behaviour during compaction and deployment is as unpredictable as those uncrimped excess fabric regions discussed above.

It is an aim of the present invention to obviate or mitigate this disadvantage of existing crimped devices.

According to a first aspect of the present invention, there is provided a crimping tool comprising:
 a mandrel having a first portion having a first outer diameter, a second portion having a second outer diameter which is greater than the first outer diameter, and a chamfered abutment face provided between the first and second portions;
 at least one first collar mountable on the first portion of the mandrel and having a chamfered first end which in use abuts the abutment face; and
 at least one second collar mountable on the second portion of the mandrel and having a chamfered second end which in use abuts the first end.

The abutment face, first end and second end may have the same chamfer angle. The "chamfer angle" is the angle of the chamfered abutment face relative to the outer surface of the first and second portions of the mandrel.

The first and second collars may be first and second inner collars and the tool may further comprise sets of concentric first and second outer collars adapted to be mounted over the respective first and second inner collars on the mandrel, each outer collar in one of the first or second set having a first or second end which abuts the first or second end of an outer collar in the other of the first and second sets when mounted on the mandrel. The respective first or second ends of the first and second outer collars are chamfered. The respective first or second ends of the first and second outer collars have the same chamfer angle as the abutment face and first and second ends of the inner collars.

According to a second aspect of the invention, there is provided a method of forming one or more crimps in a piece of fabric, the method comprising the steps of:
 providing a mandrel having a first portion having a first outer diameter, a second portion having a second outer diameter which is greater than the first outer diameter, and a chamfered abutment face provided between the first and second portions;
 forming an aperture in the piece of fabric, the aperture having a diameter which is substantially identical to the first outer diameter of the mandrel; sliding the first portion of the mandrel into the aperture until the fabric abuts the abutment face;
 providing at least one first collar having a first end which is chamfered, and at least one second collar having a second end which is chamfered; mounting the at least one first collar on the first portion of the mandrel such that the first end abuts the abutment face and traps a portion of the fabric between the chamfered abutment face and first end;
 folding the fabric over the first collar towards the first portion of the mandrel;
 mounting the at least one second collar on the second portion of the mandrel such that the second end abuts the first end and traps a further portion of the fabric between the first and second ends; and
 heat setting the fabric whilst trapped between the abutment face and first and second collars.

The first and second collars may be first and second inner collars, and prior to heat setting the method may further comprise the steps of:
 (a) providing sets of concentric first and second outer collars for mounting over the respective first and second inner collars on the mandrel, each outer collar having a chamfered first or second end;

(b) folding the fabric over the second inner collar towards the second portion of the mandrel;

(c) mounting a first outer collar on the first inner collar such that the first end of the first outer collar abuts the second end of the second inner collar and traps a further portion of the fabric between the first outer collar and second inner collar;

(d) folding the fabric over the first outer collar towards the first portion of the mandrel;

(e) mounting a second outer collar on the second inner collar such that the second end of the second outer collar abuts the first end of the first outer collar and traps a further portion of the fabric between the first and second outer collars; and repeating steps (c) to (e) with additional first and second outer collars until the desired number of crimps have been formed.

The chamfer angle of the abutment face, first end and second end may be the same.

The piece of fabric may be conical.

The step of heat setting may comprise a process selected from the following group: immersion in boiling water, heating in an oven, and steaming in an autoclave.

A preferred embodiment of the present invention will now be described, by way of example only, with reference to the following drawings.

Figure 1:
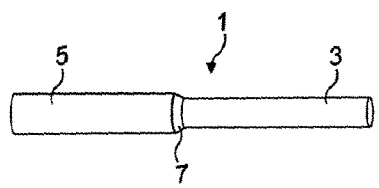
FIGS. 1-13 are perspective views of a crimping tool and the sequence of steps employed in order to crimp a fabric cone using the tool.

FIG. 1 shows a mandrel 1 which forms part of a crimping tool. In this preferred embodiment the mandrel 1 is formed from stainless steel, grade 316, although other suitable materials may be employed such as a ceramic or alloy. The mandrel 1 is made up of a first portion 3 and a second portion 5. The first portion 3 has a first outer diameter and the second portion 5 has a second outer diameter which is greater than the first outer diameter. The different outer diameters of the first and second portions 3,5 mean that an abutment face, or step, 7 is defined where the first and second portions 3,5 meet. The abutment face 7 is chamfered with a chamfer angle relative to the outer surface of the first and second portions 3,5 of the mandrel 1. The chamfer angle is preferably between 30° and 60°, and is most preferably 45°.

Figure 2:
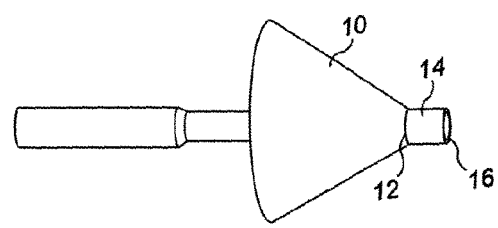

FIG. 2 shows a fabric cone 10 which is to be crimped by the crimping tool. The cone 10 may be formed by cutting a fabric sheet into the desired shape and then sewing the edges of the shape together to form the cone. Alternatively, the fabric may be weaved into a conical shape in a known manner.

Figure 3:
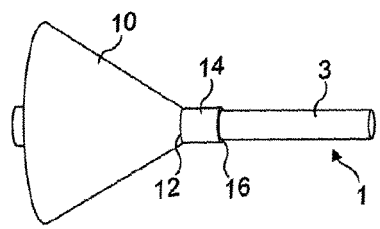

The cone is preferably formed from polyester, but may also be formed from other suitable materials such as, for example, polypropylene or polyethylene yarn. The cone 10 has a top 12 from which a cylindrical portion 14 axially extends. The cylindrical portion 14 includes an aperture 16. As can be seen in FIG. 3, the cone 10 is slid base-first onto the first portion 3 of the mandrel 1 such that the first portion 3 enters the aperture 16 and cylindrical portion 14 of the cone 10. The inner diameter of the cylindrical portion 14 is substantially identical to the first outer diameter of the first mandrel portion 3, or may be between 0.1 mm and 0.5 mm greater than the first outer diameter, such that there is a sliding fit between the two. The cone 10 is slid onto the mandrel 1 until the top 12 of the cone 10 abuts against the abutment surface 7, which is the position shown in FIG. 3.

Figure 4:
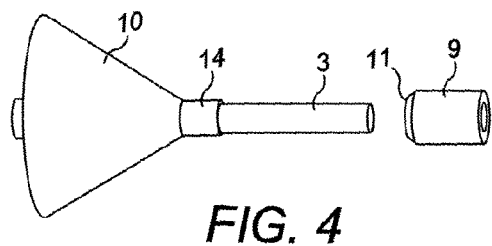
Figure 5:
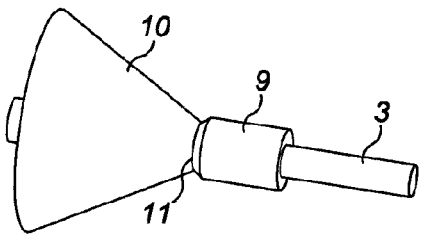
Figure 6:
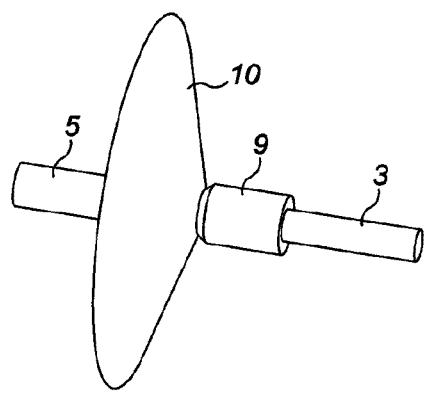
Figure 7:
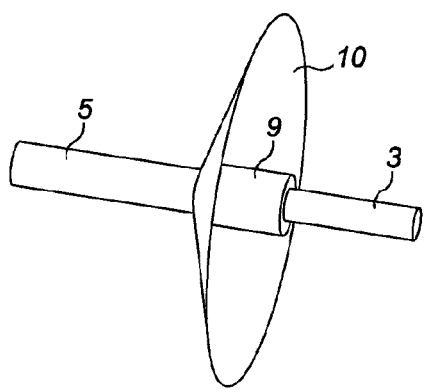
Figure 8:
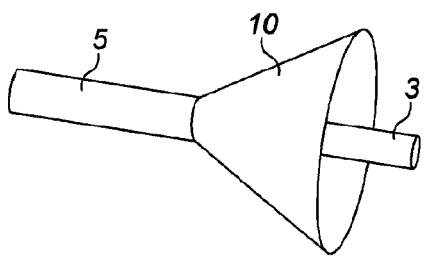

FIGS. 4 and 5 show the introduction of a first inner collar 9 forming part of the crimping tool. The first inner collar 9 is cylindrical and formed from grade 316 stainless steel. It has a proximal end 11 which is chamfered with the same chamfer angle as that of the mandrel abutment face 7. The first inner collar 9 has an inner diameter which allows the collar 9 to be mounted on the first mandrel portion 3 and over the cylindrical cone portion 14 before abutting against the abutment face 7. A portion of the fabric cone 10 is thus trapped between the abutment face 7 and the first end 11 of the first inner collar 9. As shown in FIGS. 6-8, the fabric cone 10 is pressed in a first axial direction towards the first mandrel portion 3 by the movement of the first inner collar 9 so that is folds over the first inner collar 9 and what was originally the inside of the cone 10 is now the outside in FIG. 8.

Figure 9:
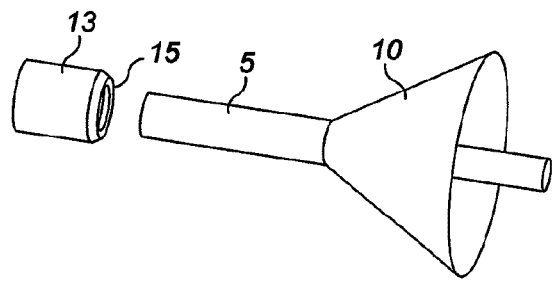
Figure 10:
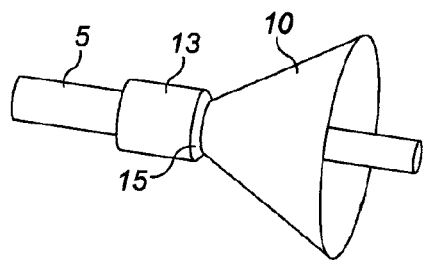
Figure 11:
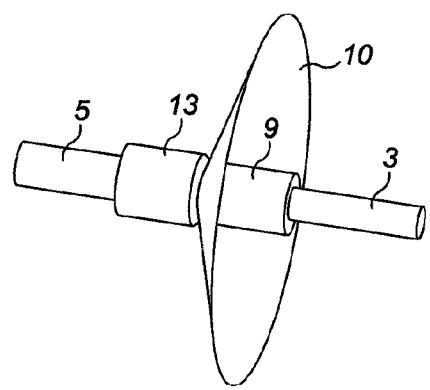
Figure 12:
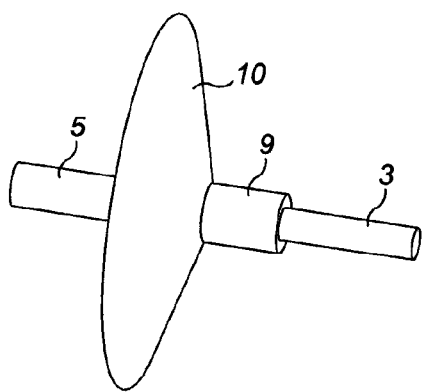
Figure 13:
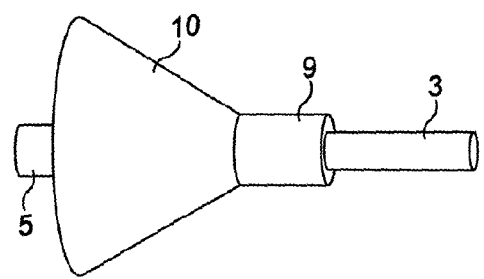

FIGS. 9 and 10 show the introduction of a second inner collar 13 forming another part of the crimping tool. As with the first inner collar 9, the second inner collar 13 is cylindrical and formed from grade 316 stainless steel. It has a proximal end 15 which is chamfered with the same chamfer angle as the aforementioned abutment face 7 and proximal end 11 of the first inner collar 9. The second inner collar 13 has an inner diameter which is larger than that of the first inner collar 9 so that the second inner collar 13 can be mounted on the larger diameter second mandrel portion 5 and abut against the proximal end 11 of the first inner collar 9. In doing so, the second inner collar 13 traps a portion of the cone 10 between itself and the first inner collar 9. As shown in FIGS. 11-13, the fabric cone 10 is then pressed in a second axial direction towards the second mandrel portion 5 so that is folds over the second inner collar 13 such that the cone 10 reverts back to the original position shown in FIGS. 2-5.

Figure 14:
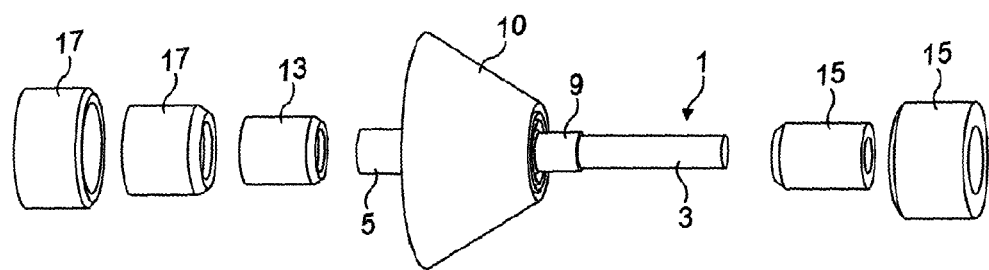
FIG. 14 is an exploded view of the various components of the crimping tool.

The overall number of collars used in the crimping tool is dependent upon the amount of fabric to be crimped, and/or the number of crimps or pleats required. FIG. 14 shows an exploded view of a preferred embodiment of the complete crimping tool. In this embodiment, the crimping tool further comprises sets of first and second outer collars 15,17 adapted to be mounted on the respective first and second inner collars 9,13 on the mandrel 1. The first and second outer collars 15,17 in each set are concentric, where each outer collar 15,17 has an inner diameter which is slightly larger than the outer diameter of its respective inner collar 9,13 or preceding outer collar 15,17. As with the inner collars 9,13 the proximal end of each outer collar is chamfered, preferably with the same chamfer angle as the mandrel abutment face 7 and proximal ends of the inner collars 9,13.

The method of crimping the fabric cone 10 continues in the same manner as already described, wherein outer collars from the first and second sets 15,17 are alternately mounted on a preceding collar so that portions of the fabric cone are trapped between respective pairs of first and second outer collars 15,17. The cone is then alternately pressed in either the first or second axial direction over a first or second outer collar 15,17 before the next collar in the sequence is added until such time as the desired number of crimps are obtained.

Once the appropriate number of inner and/or outer collars have been added they are preferably secured to the mandrel by a locking ring (not shown) or alternatively a grub screw or collet. The cone 10 is then ready for heat treatment in order to set the crimps defined by the crimping tool. Setting the crimps can be achieved in several ways. The tool and cone may be immersed in boiling water at substantially 100° C. Alternatively, they may be treated with dry heat in an oven at a temperature in the range 100-160° C., or else treated with steam in an autoclave at approximately 130° C. The duration of the heat treatment will be dependent upon the method of treatment selected, but will be between 5 and 30 minutes.

Figure 15:
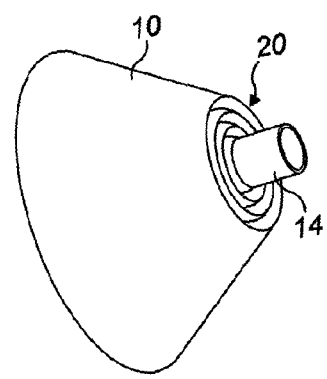
FIG. 15 is a perspective view of a fabric cone crimped using the crimping tool.

Following the heat treatment the collars are removed and the finished product can be taken from the mandrel. An example of a finished product is shown in FIG. 15, where an area 20 of concentric crimps is visible immediately below the cylindrical portion 14 at the top of the cone 10.

The tool and method of the present invention ensure uniformity of crimps or pleats in a piece of fabric, whether for use in a medical device or elsewhere. They also ensure that the crimps or pleats can be set manually in a quick and straightforward manner, thus increasing productivity.

Whilst the illustrated preferred embodiment of the invention is described for producing a medical device such as a cardiovascular stent graft, the invention is not limited to the production of such devices. The tool and process could also be used for forming other crimped fabric items such as, for example, fabric filter elements for water filters.

Whilst the fabric to be crimped is preferably formed in a cone shape prior to crimping, it may alternatively be provided in the shape of a disc with a central aperture for the mandrel to slide through. The crimps can then be set in the same manner as described above.

Whilst it is preferred that the tool comprises first and second sets of outer collars, the tool may in certain circumstances only comprise first and second inner collars in the event that only a single crimp or pleat is desired.

These and other modifications and improvements may be incorporated without departing from the scope of the present invention.

The invention claimed is:

1. A crimping tool comprising:
   a mandrel comprising a first portion having an outer surface defining a first outer diameter, a second portion having an outer surface defining a second outer diameter which is greater than the first outer diameter, and an outer chamfered abutment face extending between the outer surfaces of the first and second portions;
   at least one first collar mountable on the outer surface of the first portion of the mandrel and having a chamfered first end which engages with the abutment face when the at least one first collar is mounted on the outer surface of the first portion; and
   at least one second collar mountable on the outer surface of the second portion of the mandrel and having a chamfered second end which engages with the first end of the at least one first collar when the at least one first and second collars are mounted on the outer surface of the second portion.

2. The tool of claim 1, wherein the abutment face, first end and second end have the same chamfer angle.

3. The tool of claim 2, wherein the first and second collars are first and second inner collars, respectively, and wherein the tool further comprises at least one first outer collar and at least one second outer collar adapted to be mounted concentrically over the first and second inner collars on the mandrel, respectively, the at least one first outer collar having a first end which engages the second end of the second inner and the at least one second outer collar having a second end which engages the first end of the first outer collar when the at least one first and second inner and outer collars are mounted on the mandrel.

4. The tool of claim 2, wherein the chamfer angle is between 30° and 60°.

5. The tool of claim 2, wherein the chamfer angle is 45°.

6. The tool of claim 1, wherein the first and second collars are first and second inner collars, respectively, and wherein the tool further comprises at least one first outer collar and at least one second outer collar adapted to be mounted concentrically over the first and second inner collars on the mandrel, respectively, the at least one first outer collar having a first end which engages the second end of the second inner collar and the at least one second outer collar having a second end which engages the at least one first end of the first outer collar when the at least one first and second inner and outer collars are mounted on the mandrel.

7. The tool of claim 6, wherein the respective first and second ends of the first and second outer collars are chamfered.

8. The tool of claim 7, wherein the respective first and second ends of the first and second outer collars have the same chamfer angle as the abutment face and the first and second ends of the inner collars.

9. The tool of claim 8, wherein the chamfer angle of the abutment face is between 30° and 60°.

10. The tool of claim 8, wherein the chamfer angle of the abutment face is 45°.

11. The tool of claim 1, wherein the mandrel is fabricated from at least one of stainless steel, a ceramic or a metal alloy.

12. The tool of claim 1, wherein the mandrel is comprised of stainless steel.

13. The tool of claim 1, wherein the at least one first collar is cylindrical and comprises an inner bore, wherein the inner bore is configured to axially slidingly engage the outer surface of the first portion.

14. The tool of claim 1, wherein the at least one second collar is cylindrical and comprises an inner bore, wherein the inner bore is configured to axially slidingly engage the outer surface of the second portion.

15. The tool of claim 1, wherein the at least one first collar and the at least one second collar are fabricated from a metal alloy.

16. The tool of claim 1, wherein the at least one first collar and the at least second collar are fabricated from stainless steel.

17. The tool of claim 1, wherein the outer chamfered abutment face comprises an angled outer surface portion of the mandrel that extends linearly between the outer surfaces of the first and second portions.

18. The tool of claim 17, wherein the chamfered first end of the at least one first collar comprises an angled surface portion which engages with the abutment face when the at least one first collar is mounted on the outer surface of the first portion, and the chamfered second end of the at least one second collar comprises an angled surface portion which engages with the first end of the at least one first collar when the at least one first and second collars are mounted on the outer surface of the second portion.

19. The tool of claim 1, wherein the at least one first collar is configured to axially slidingly engage with the outer surface of the first portion.

20. The tool of claim 1, wherein the at least one second collar is configured to axially slidingly engage with the outer surface of the second portion.

21. The tool of claim 1, wherein the chamfered first end of the at least one first collar comprises an outer portion and an inner portion that engages with the abutment face when the least one first collar is mounted on the outer surface of the first portion, and wherein the abutment face comprises an angled outer surface that is angled outwardly as is extends axially in a direction extending from the first portion to the second portion and the outer portion of the chamfered first end comprises an angled outer surface that is angled outwardly as is extends axially in a direction extending from the second portion to the first portion.

22. The tool of claim 21, wherein the chamfered second end of the at least one second collar comprises an outer portion and an inner portion that engages with the outer portion of the chamfered first end of the at least one first collar when the least one first and second collars are mounted on the outer surfaces of the first portion and second portions, respectively, and wherein the outer portion of the at least one second collar comprises an angled outer surface that is angled outwardly as is extends axially in a direction extending from the first portion to the second portion.

23. The tool of claim 1, wherein the at least one first collar is mounted on the outer surface of the first portion of the mandrel with the chamfered first end thereof engaged with the abutment face, and the at least one second collar is mounted on the outer surface of the second portion of the mandrel with the chamfered second end thereof engaged with the first end of the at least one first collar.

24. The tool of claim 23, wherein the chamfered first end of the at least one first collar is indirectly engaged with the abutment face, and the chamfered second end of the at least one second collar is indirectly engaged with the first end of the at least one first collar.

25. The tool of claim 24, further comprising a piece of fabric having an aperture having a diameter which is substantially identical to the first outer diameter of the mandrel, and wherein the fabric is mounted on the first portion of the mandrel via the aperture such that the fabric abuts the abutment face, wherein a portion of the fabric is trapped between the abutment face and the first end of the at least one first collar and the fabric extends over the first collar towards the first portion of the mandrel, and wherein a portion of the fabric is trapped between the first end of the at least one first collar and the second end of the at least one second collar.

26. A method of forming one or more crimps in a piece of fabric, the method comprising the steps of:
 providing a mandrel having a first portion with an outer surface defining a first outer diameter, a second portion with an outer surface defining a second outer diameter which is greater than the first outer diameter, and an outer chamfered abutment face extending between the outer surfaces of the first and second portions;
 forming an aperture in the piece of fabric, the aperture having a diameter which is substantially identical to the first outer diameter of the mandrel;
 sliding the first portion of the mandrel into the aperture until the fabric abuts the abutment face;
 providing at least one first collar having a first end which is chamfered, and at least one second collar having a second end which is chamfered;
 mounting the at least one first collar on the outer surface of the first portion of the mandrel such that the first end engages the abutment face and traps a portion of the fabric between the outer chamfered abutment face and the first end;
 folding the fabric over the first collar towards the first portion of the mandrel;
 mounting the at least one second collar on the outer surface of the second portion of the mandrel such that the second end engages the first end and traps a further portion of the fabric between the first and second ends; and
 heat setting the fabric whilst trapped between the abutment face and the first and second collars.

27. The method of claim 26, wherein the first and second collars are first and second inner collars, and prior to heat setting the method further comprises the steps of:
 providing at least one set of concentric first and second outer collars for mounting over the first and second inner collars, respectively, on the mandrel, each outer collar having a chamfered end;
 folding the fabric over the second inner collar towards the second portion of the mandrel;
 mounting a first outer collar of the at least one set of concentric first and second outer collars on the first inner collar such that the chamfered end of the first outer collar engages the second end of the second inner collar and traps a further portion of the fabric between the first outer collar and the second inner collar;
 folding the fabric over the first outer collar towards the first portion of the mandrel; and
 mounting a second outer collar on the second inner collar such that the chamfered end of the second outer collar abuts the chamfered end of the first outer collar and traps a further portion of the fabric between the first and second outer collars.

28. The method of claim 26, wherein the chamfer angle of the abutment face, first end and second end are the same.

29. The method of claim 26, wherein the piece of fabric is conical.

30. The method of claim 26, wherein the step of heat setting comprises a process selected from the following group: immersion in boiling water, heating in an oven, and steaming in an autoclave.

31. The method of claim 27, wherein the chamfer angle of the abutment face, first end and second end may be the same.

32. The method of claim 27, wherein the piece of fabric is conical.

33. The method of claim 28, wherein the piece of fabric is conical.

34. The method of claim 27, wherein the step of heat setting comprises a process selected from the following group: immersion in boiling water, heating in an oven, and steaming in an autoclave.

35. The method of claim 28, wherein the step of heat setting comprises a process selected from the following group: immersion in boiling water, heating in an oven, and steaming in an autoclave.

36. The method of claim 29, wherein the step of heat setting comprises a process selected from the following group: immersion in boiling water, heating in an oven, and steaming in an autoclave.

37. The method of claim 31, wherein the piece of fabric is conical.

38. The method of claim 31, wherein the step of heat setting comprises a process selected from the following group: immersion in boiling water, heating in an oven, and steaming in an autoclave.

39. The method of claim 33, wherein the step of heat setting comprises a process selected from the following group: immersion in boiling water, heating in an oven, and steaming in an autoclave.

* * * * *